United States Patent [19]

Feldsine et al.

[11] Patent Number: 5,658,747
[45] Date of Patent: Aug. 19, 1997

[54] COMPOSITIONS AND METHODS FOR CONTROL OF REACTIVITY BETWEEN DIAGNOSTIC REAGENTS AND MICROORGANISMS

[75] Inventors: Philip T. Feldsine, Mercer Island; Sharon L. Brunelle, Redmond; Maria T. Falbo-Nelson, Everett; Dennis M. Scully, Edmonds, all of Wash.

[73] Assignee: BioControl System, Inc., Bothell, Wash.

[21] Appl. No.: 240,157

[22] Filed: May 10, 1994

[51] Int. Cl.⁶ .................. G01N 33/554; G01N 33/569; G01N 21/00; G01N 31/00
[52] U.S. Cl. ................. 435/7.32; 435/7.35; 435/7.37; 435/7.92; 435/7.94; 435/7.1; 435/7.2; 422/55; 422/48; 436/17; 436/524
[58] Field of Search .................. 252/408.1; 422/55–58; 435/5, 7.1, 7.2, 7.32, 7.35, 7.37, 7.92, 7.94, 963, 970, 971; 436/17, 18, 176, 524, 527, 826

[56] References Cited

U.S. PATENT DOCUMENTS

Re. 34,405  10/1993  Gould et al. ................ 435/7.1
4,632,901  12/1986  Valkirs et al. .
4,727,019   2/1988  Valkirs et al. .
4,855,240   8/1989  Rosenstein et al. .
4,859,604   8/1989  Vulimiri et al. .
4,861,711   8/1989  Friesen et al. .
4,943,522   7/1990  Eisinger et al. .
5,120,643   6/1992  Ching et al. ................ 435/7.92

FOREIGN PATENT DOCUMENTS 2204398    11/1988  United Kingdom ......... G01N 33/532
2262986     7/1993  United Kingdom ......... G01N 33/53
WO 92/21980 12/1992  WIPO .................. G01N 33/56
WO 9303175  2/1993  WIPO .................. C12Q 1/00

Primary Examiner—James C. Housel
Assistant Examiner—Jennifer Shaver
Attorney, Agent, or Firm—Seed and Berry LLP

[57] ABSTRACT

Compositions, devices and methods for the detection of target microorganisms, such as by a visual immunoprecipitation assay, where the detection requires the migration of the target microorganisms (typically a target microorganism-antibody-detection reagent complex) along a lateral flow membrane of a diagnostic device. The present invention permits such detection by inhibiting the agglutination, or other aggregation, of target microorganisms (and particularly target microorganisms bound to an antibody-detection reagent) while the microorganisms are migrating along the lateral flow membrane.

**14 Claims, 1

COMPOSITIONS AND METHODS FOR CONTROL OF REACTIVITY BETWEEN DIAGNOSTIC REAGENTS AND MICROORGANISMS

TECHNICAL FIELD

The present invention relates to compositions and methods for the control of the degree of reactivity between microbiological organisms and labeled antibodies to reduce agglutination of complexes between the two.

BACKGROUND OF THE INVENTION

Microbial diseases have long been a major health concern worldwide. A key feature in the prevention of such diseases is early diagnosis. Epidemiologists must look for microbial contamination in the environment as well as in food products to find common causes of outbreaks.

One example is the outbreak in 1992 of Enterohemorrhagic E. coli (EHEC) in the Pacific Northwest of the United States due to contaminated ground beef. EHEC is a relatively "newly discovered" pathogen. EHEC was first isolated in 1975, and it was not until 1982 that E. coli 0157:H7 was associated with two food-related outbreaks of hemorrhagic colitis in the United States. The reported incidence of E. coli 0157:H7 cases is increasing. Typically, E. coli strains are harmless commensals, but a few strains are pathogenic. EHEC is particularly virulent and can trigger deadly complications, including severe abdominal cramps and acute renal failure in children as well as cardiovascular and central nervous system problems.

As another example, Salmonella is the leading cause (more than 50%) of total bacterial foodborne disease outbreaks, according to the United States Centers for Disease Control (CDC) surveillance of foodborne diseases. On average, there were 68 incidents and 6249 cases per year reported to the CDC during the period 1983–1987, the most recent summary period available. Salmonella can infect a broad variety of warm- and cold-blooded animals, and can survive for long periods of time outside a host.

Listeria, a genus of gram positive bacteria, is widely distributed in nature, having been isolated from soil, water, vegetation and many animal species. Serious outbreaks of human listeriosis have not been frequent, but have been identified with increasing incidence. In addition, the detection frequency for Listeria in the agricultural environment appears to be increasing. For specific outbreaks of listeriosis, estimates place mortality at 30% to 40% of affected patients, however, little is known of the minimum infective dose. One particularly troublesome aspect of Listeria control in foods is that Listeria can grow at temperatures as low as −0.4° C. and as high as 44° C. These factors all contribute to the increasing significance of Listeria as a food pathogen.

The ability to monitor potential environmental and food sources of microbial contamination quickly and easily would reduce the risk of human infection and potential mortality. A device able to assay for microorganisms, including bacteria, yeasts, molds, fungi, parasites and viruses, that requires no special or technical equipment, can be performed in the field and does not require special skills would be useful for diagnosis as well as environmental monitoring and food sampling. In the case of foodborne bacterial contamination, three of the major disease-related organisms are Salmonella, Listeria and EHEC.

There are a number of Salmonella, Listeria, and EHEC detection methods presently available. Trained laboratory technicians and a minimum of 2–5 days are required to obtain evidence of these organisms by the standard cultural methods of analysis. New, more rapid methods are based on such techniques as enzyme immunoassay (EIA), DNA hybridization, immunodiffusion, or growth/metabolism measurements. While taking much less time than the cultural methods, these rapid tests still require skilled technical training, a functional laboratory, and specialized equipment. These tests generally take two or more days total, including several hours of hands-on time. When looking at other developing technologies in the diagnostics field, such as flow cytometry and polymerase chain reaction (PCR), the instrumentation and technical skills that are required to accurately perform such tests render them inappropriate for use in food microbiology, environmental testing and physician's office diagnosis.

Another recent technology in the diagnostics field involves lateral flow sandwich immunoassays. Such tests have been developed for the detection of human chorionic gonadotropin (hCG), and applied to pregnancy testing. Typically, a monoclonal or polyclonal antibody is mobilized in a discrete band near the distal end of a solid carder strip, called the detection zone. Another mount of antibody is labeled with a detection reagent such as an inorganic sol or dyed polystyrene particle. This labeled antibody is reversibly fixed near the proximal end of the carrier strip. Upon hydration of the proximal end with a sample fluid potentially containing the antigen, the antigen reacts with the labeled antibody and the complex passes through the zone of mobilized antibody, forming a sandwich upon reacting with the immobilized antibody. The capture of the chromogenic reagent-antigen complex causes the formation of a visible signal in the detection zone.

There are at least two major challenges that must be addressed to distinguish pathogenic bacteria, as opposed to distinguishing hormones or other soluble molecular targets. These challenges are the need to detect all of the target strains of a target microorganism in the presence of numerous antigenically related organisms, with a low tolerance for false positive results and a very low, preferably zero, tolerance for false negatives, and the physical size and heterogeneity of the target itself. A typical clinical diagnostic test, such as a test for hCG in urine, is focused on detecting a single, small, unique entity (i.e., a hormone) in a well-characterized matrix (e.g., urine). Furthermore, the structure of the analyte (hCG), is defined and uniform in size and composition.

Pathogen detection, for example, a test for E. coli 0157:H7, must distinguish a particular pathogenic strain from nonpathogenic strains of the target microorganism. In contrast to the well-defined small size and structure of most hormones or marker proteins, microorganisms are very large and their surfaces are heterogeneous and can undergo changes, such as the phase-switching of Salmonella flagella.

In previous attempts to transfer the lateral flow technology of clinical chemistry to the detection of microorganisms, high affinity polyclonal antibodies were prepared against Salmonella, Listeria, and EHEC antigens. These antibodies were conjugated to chromogenic reagents such as dyed polystyrene particles and inorganic sols. Upon addition of the target microorganisms, rapid and pronounced agglutination occurred, resulting in large aggregates that prevented the flow of the chromogenic reagent-analyte complex along the solid carrier to the zone of capture antibody.

Thus, there is a need in the art for the adaptation of lateral flow technology for the detection of heterogeneous microorganisms in a variety of matrices. The present invention provides these and other, related advantages.

SUMMARY OF THE INVENTION

The present invention provides for the detection of target microorganisms, such as by a visual immunoprecipitation assay, by use of a lateral flow diagnostic device. The present invention permits such detection by inhibiting the agglutination, or other aggregation, of target microorganisms (and particularly antibody-bound target microorganisms) while the microorganisms are migrating along a lateral flow of the detection device. The present invention inhibits such agglutination by providing a composition that is believed to encapsulate and stabilize antibody-detection reagents in the reagent zone of the lateral flow diagnostic device, and then assist antibody-detection reagent-target microorganism complexes to flow downstream out of the reagent zone and along the lateral flow membrane, without agglutination, to a detection zone where an mobilized antibody capable of specifically binding the complex is located.

In one aspect, the present invention provides a composition for use in an assay to detect a target microorganism wherein the composition comprises about 0.1% to about 60% by weight of a polyol, up to about 25% by weight of a protein, about 0.1% to about 10% by weight of a gelatin, and an antibody-detection reagent capable of specifically binding to the target microorganism. In a preferred embodiment, the composition further comprises up to about 2% by weight of a detergent, preferably a non-ionic detergent, further preferably selected the group consisting of Tween 20 and Triton X100.

In a preferred embodiment, the polyol is a saccharide polyol, and is selected from the group consisting of sucrose, polyethylene glycol and dextrose, and further preferably is sucrose. In another preferred embodiment, the protein is an inert protein that is non-reactive towards the target microorganism and the antibody specific for the target microorganism, and is further preferably selected from the group consisting of bovine serum albumin, other albumins, and casein. In yet another preferred embodiment, the gelatin is a high molecular weight gelatin, and further preferably comprises fish skin gelatin. The detection reagent that is bound to the target microorganism-specific antibody is preferably a dyed polystyrene or an inorganic sol such as colloidal gold.

It is a feature of this aspect of the present invention that the composition can be located in a reagent zone of a lateral flow device for the detection of the target microorganism, the device comprising a lateral flow membrane having the reagent zone and a detection zone. The detection zone has an immobile binding partner capable of binding a complex formed by the target microorganism, the antibody specific to the microorganism and the detection reagent and is located downstream of the reagent zone.

In preferred embodiments, the compositions, the detection devices, and the methods of detecting are specific for Listeria, Enterohemorrhagic *E. coli* (EHEC), or Salmonella.

In another aspect, the present invention provides a lateral flow device, or detection device, for the detection of a target microorganism. The lateral flow device comprises a lateral flow membrane having a reagent zone comprising a porous, non-absorbent pad containing a composition as described above, typically comprising about 0.1% to about 60% by weight of a polyol, up to about 25% by weight of a protein, about 0.1% to about 10% by weight of a gelatin and an antibody-detection reagent capable of specifically binding to the target microorganism. The porous, non-absorbent pad has a pore size greater than the size of a complex between the target microorganism and the antibody-detection reagent. The lateral flow device also has a detection zone located downstream of the reagent zone, the detection zone comprising an immobile binding partner capable of specifically binding the complex between the target microorganism and the antibody-detection reagent.

In a preferred embodiment, the lateral flow device further comprises an absorbent pad capable of absorbing fluid on the lateral flow membrane and located downstream of the detection zone. Preferably, the lateral flow membrane comprises nitrocellulose or nylon.

In yet another aspect, the present invention provides methods of detecting a target microorganism comprising contacting a sample potentially containing the target microorganism with a composition as described above located in a reagent zone of a lateral flow membrane under conditions that permit the antibody-detection reagent to bind to the target microorganism to provide a complex between the target microorganism and the antibody-detection reagent. Then, the complex migrates downstream along the lateral flow membrane to a detection zone containing an immobile antibody capable of binding to the complex to provide a bound complex. Next, the bound complex is detected.

In a preferred embodiment, the sample is a solution comprising a field sample, and the method further comprises adding the sample to a porous, non-absorbent pad located in the reagent zone, the porous pad having a pore size greater than the size of the complex between the target microorganism and the antibody-detection reagent, and detritus is filtered from the field sample prior to the migrating. Further preferably, the field sample is selected from the group consisting of a food sample, an environmental sample such as dirt or water and a biological fluid sample.

These and other aspects of the present invention will become evident upon reference to the following detailed description, examples and attached drawings.

BRIEF DESCRIPTION OF THE DRAWINGS

FIG. 1A depicts in stylistic form the device prior to the addition of a sample to the reagent pad of the device. FIG. 1B depicts in stylistic form the device after the sample has migrated downstream along the device across the detection zone and into the absorbent pad.

DETAILED DESCRIPTION OF THE INVENTION

Figure 1A:
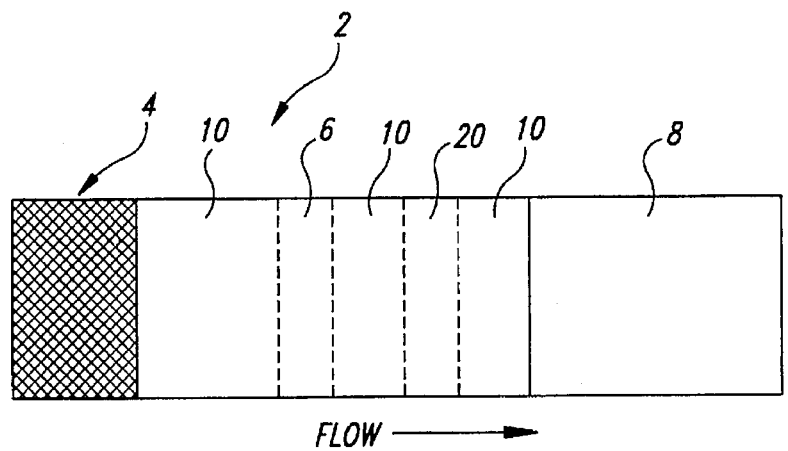
FIGS. 1A and 1B depict a top view of a lateral flow diagnostic device according to the present invention.

The present invention is directed toward the detection of target microorganisms, such as by a visual immunoprecipitation assay, where the detection requires the migration of the target microorganisms (typically a target microorganism-antibody-detection reagent complex) along a lateral flow membrane of a diagnostic device. The present invention permits such detection by inhibiting the agglutination, or other aggregation, of target microorganisms (and particularly antibody-bound target microorganisms) while the microorganisms are migrating along the lateral flow membrane.

The present invention inhibits such agglutination by providing a composition that is believed to initially encapsulate and stabilize the antibodies in the reagent zone of the lateral flow diagnostic device, which capsules are then dehydrated onto the reagent zone. The antibodies are attached to a detection reagent, such as a dyed polystyrene particle or colloidal gold, or are otherwise labeled. Subsequently, upon addition of a sample potentially containing the target microorganism, the composition and antibody are rehydrated and binding between the antibody and the target microorganism is permitted, thereby forming an antibody-detection reagent-target microorganism complex. Next, the complex is assisted by the inventive composition to flow downstream out of the reagent zone and along the lateral flow membrane, without agglutination, to a detection zone where an immobilized antibody capable of specifically binding the complex is located. Unbound antibody proceeds to an absorbent pad located further downstream from the detection zone.

The present invention also inhibits such agglutination by providing a preferred lateral flow diagnostic device wherein a glass fiber pad, or other porous and non-absorptive pad, is located at the reagent zone. The glass fiber pad is impregnated with the inventive composition combined with an antibody-detection reagent specific for the target microorganism. The impregnated glass fiber pad provides an important filtering effect to remove undesirable detritus such as bits of food or other material present in the sample, which is typically a field sample that has not been purified prior to its application to the diagnostic device. The glass fiber pad accepts a significant amount of sample, filters the sample, and releases the sample to the lateral flow membrane without retaining (e.g., absorbing) significant amounts of the sample, or microorganisms in the sample. The glass fiber pad has a pore size that is larger than the target microorganism, preferably 500 to 1000 times or more greater in diameter than the target microorganism.

Thus, in one aspect the present invention provides a composition for use with a lateral flow diagnostic device for the detection of a target microorganism. The target microorganism is preferably a whole microorganism, but may also be cellular debris and/or lysed cells. The composition generally comprises from about 0.1 to about 60% by weight of a polyol, typically from about 1 to about 40% by weight of a polyol, and preferably from about 2 to about 15% by weight of a polyol. The polyol is preferably a saccharide polyol, and is further preferably selected from the group consisting of sucrose, polyethylene glycol and dextrose, and is still further preferably sucrose. The composition also generally contains from 0 to about 25% by weight of a protein, typically from about 0.1 to about 10% by weight of a protein, and further preferably from about 0.5 to about 2% by weight of a protein. The protein is preferably an inert protein that is non-reactive towards the target microorganism or antibody, and is further preferably selected from the group consisting of bovine serum albumin (BSA), other albumins, and casein. Further preferably, the protein is BSA. The composition also generally contains from 0.1 to about 10% by weight of a gelatin, typically from about 0.15 to about 5% by weight of a gelatin, and further preferably from about 0.2 to about 1% by weight of a gelatin. Preferably, the gelatin is a high molecular weight gelatin such as fish skin gelatin. In a preferred embodiment, the present invention does not include pyrrole, pyrrolidone, or other pyrrole-related compounds.

In an alternative embodiment, the composition also generally contains up to about 10% by weight of a detergent, typically up to about 2% by weight, and preferably up to about 0.5% by weight. The detergent is preferably a non-ionic detergent, and is further preferably selected from the group consisting of Tween 20 and Triton X100. The components of the composition are mixed together with an antibody-detection reagent specific for a target microorganism prior to application of the mixture to the reagent zone of the diagnostic device (of course, the components and the diagnostic device may be in an alternative order, if desired).

Within the context of the present invention, the term "antibody" includes a polyclonal antibody, monoclonal antibody, anti-idiotypic antibody, fragments thereof such as F(ab')$_2$ and Fab fragments and a recombinantly produced binding partner. The antibody, including the "antibody-detection reagent" initially located in the reagent zone, is typically either a polyclonal or monoclonal antibody, and is preferably a polyclonal antibody. Further, the polyclonal antibody is preferably affinity column purified prior to its utilization in the present invention. The production of such antibodies is well known in the art. (See, e.g., *Antibodies: A Laboratory Manual*, Harlow and Lane (eds.), Cold Spring Harbor Laboratory Press, 1988; this reference, and all other references cited herein, is expressly incorporated herein by reference in its entirety.) Suitable affinity purified antibodies can also be commercially available. For example, a polyclonal antisera specific for Listeria is available from Kirkegaard and Perry Laboratories, Gaithersburg, Md.

A polyclonal antibody can be readily generated by one of ordinary skill in the art via immunization of a variety of warm-blooded animals such as horses, cows, goats, sheep, dogs, chickens, turkeys, rabbits, mice, or rats. Briefly, the target microorganism, or an antigen specifically associated with the target microorganism, is utilized to immunize the animal. The immunogenicity of the protein or peptide of interest may be increased through the use of an adjuvant such as Freund's complete or incomplete adjuvant or by coupling to another protein such as ovalbumin or keyhole limpet hemocyanin (KLH).

A monoclonal antibody can also be readily generated using well-known techniques. (See, e.g., *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), supra.) Briefly, as one example, a subject animal is immunized as with the production of a polyclonal antibody. Alternatively, in vitro immunization techniques suitable for the production of monoclonal antibodies are also known in the art. Antibody-producing cells are then fused to immortal myeloma cells to provide an immortal hybridoma cell line. Following the fusion, the cells are placed into culture plates containing a suitable medium, traditionally HAT medium, although other suitable media are known in the art. After about seven days, the resulting fused cells or hybridomas may be screened in order to determine the presence of antibodies which recognize the desired antigen. Following several clonal dilutions and reassays, hybridoma producing antibodies that bind to the protein of interest can be isolated.

Other techniques can also be utilized to construct monoclonal antibodies or binding partners. (See, e.g., Huse et at., "Generation of a Large Combinational Library of the Immunoglobulin Repertoire in Phage Lambda," *Science* 246:1275–1281, 1989; Sastry et at., "Cloning of the Immunological Repertoire in *Escherichia coli* for Generation of Monoclonal Catalytic Antibodies: Construction of a Heavy Chain Variable Region-Specific cDNA Library," *Proc. Natl. Acad Sci. USA* 86:5728–5732, 1989; Alting-Mees et al., "Monoclonal Antibody Expression Libraries: A Rapid Alternative to Hybridomas," *Strategies in Molecular Biology* 3:1–9, 1990; Larrick et al., "Polymerase Chain Reaction Using Mixed Primers: Cloning of Human Monoclonal Antibody Variable Region Genes From Single Hybridoma Cells," BioTechnology 7:934–938, 1989.)

Once a suitable antibody has been obtained, it may be isolated or purified by many techniques well known to those of ordinary skill in the art (see *Antibodies: A Laboratory Manual*, Harlow and Lane, supra).

The antibodies are preferably capable of selectively detecting all of the strains of a target microorganism in the presence of numerous antigenically related organisms. Further, the antibodies are preferably capable of such detection with a low tolerance for non-specific binding (which leads to a false positive result) and a very low, preferably zero, failure to bind target the microorganism (which leads to a false negative result).

Typically, the antibody-detection reagent that is mixed with the inventive composition is a label. Preferably, the label is bound to the antibody without significantly interfering with the antibody reagent's ability to specifically bind to the target microorganism. In preferred embodiments, the detection reagent is a dyed polystyrene particle or an inorganic sol with a diameter of 5 nm to 500 nm. Where the detection reagent is a sol, the detection reagent is preferably a colloidal gold particle. Alternative chromogenic reagents and other detectable labels are well known in the art and, although lesser preferred, are suitable for use within certain aspects of the present invention. Typically, the complex will be detectable because the target specific antibody is attached to a chromogenic reagent. But, the binding of the antibody-detection reagent to the immobilized antibody may also provide for a detectable event, or the solid phase bound, immobile antibody or the complex may be otherwise labeled. Examples of labels may be found in U.S. Pat. No. 4,861,711 and U.S. Pat. No. 4,859,604.

It is a feature of the present invention that the target microorganism can be a whole microorganism, and may be a live microorganism. Further, it is a feature of the present invention that the target microorganism can be cellular debris and/or lysed cells The target microorganism is preferably a bacteria, although any single cell entity capable of existence in the field or in a sample is acceptable. For example, in preferred embodiments the microorganism comprises a microorganism capable of existence in a field sample, such as a yeast, bacterium, mold, fungi, parasite or virus. Alternatively, although lesser preferred, the microorganism is actually a cell, such as a eukaryotic cell such as a red blood cell, or tissue cell from an animal. The pore diameter of the porous material located in the preferred reagent zone is selected to accommodate the size of the target microorganism.

In a further aspect, the present invention provides a preferred lateral flow diagnostic device suitable for detection of a target microorganism. As depicted in FIG. 1, the lateral flow diagnostic device 2 comprises a lateral flow membrane 10 having a reagent zone 4 that is usually located at or near a first end of the diagnostic device 2. Adjacent to reagent zone 4 is preferably a portion of the lateral flow membrane 10 that does not contain porous pad or immobilized antibody, followed by a detection zone 6 comprising an immobilized antibody that is capable of binding the target microorganism-antibody-detection reagent complex (the complex is, in certain embodiments, also known as an antibody-bound target microorganism). The immobilized antibody (also known as a capture antibody) is typically bound to the lateral flow membrane, but may be bound to another solid phase or otherwise immobilized. Preferably, the lateral flow membrane 10 is a strip of nitrocellulose, nylon or a similar, porous material having low absorbency suitable for the migration and/or transmission of microorganisms. The pores of the lateral flow membrane, where present, are typically about 5–10 times greater in diameter than the target microorganism. Although lesser preferred, the lateral flow membrane can also be non-porous, highly absorbent, non-absorbent or adsorbent, provided such properties do not prevent the lateral flow of the target microorganism-antibody-detection reagent complex and do not prevent detection of the target microorganism at the detection zone 6.

Figure 1B:
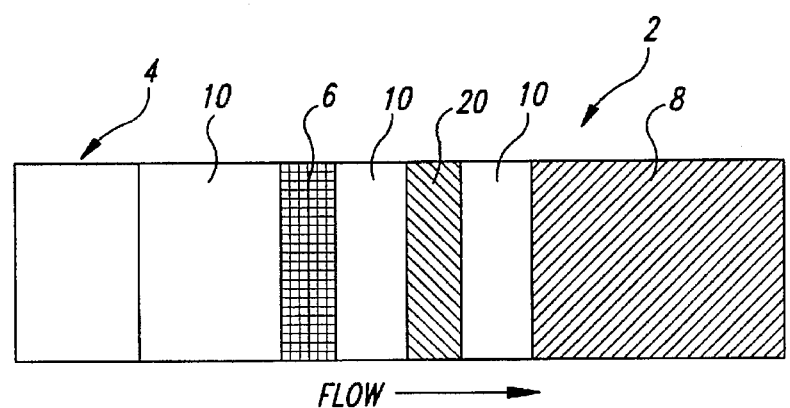

FIG. 1A depicts in stylistic form the appearance of the device before the addition of a sample to the reagent zone 4, with the sample located principally in the reagent zone 4. FIG. 1B stylistically depicts the device after the fluid from the sample has migrated across the lateral flow membrane 10, passed through the detection zone 6, migrated along further lateral flow membrane 10, and then has been absorbed into absorbent pad 8.

Figure 2:
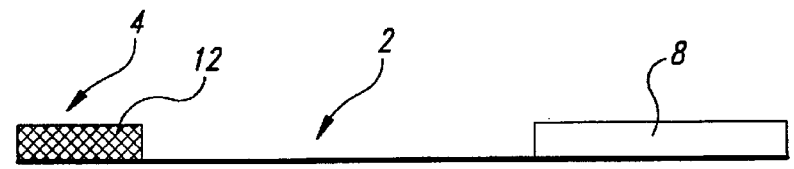
FIG. 2 depicts a side view of the lateral flow diagnostic device of the present invention.

As depicted in FIG. 2, the reagent zone 4 of the diagnostic device preferably comprises a porous pad 12 on which is dried the composition and antibody-detection reagent of the invention. The porous pad 12 is capable of accepting a significant amount of a sample and then filtering and releasing the sample to the lateral flow membrane. The porous pad 12 is a loosely woven or non-woven material or mesh, and is not absorbent, although in lesser preferred embodiments the porous pad 12 can be an absorbent material if the pore size of the absorbent material is adequate and there is adequate sample for total saturation of the resulting absorbent reagent zone. Preferably, the porous pad 12 is a glass fiber pad. The inclusion of porous pad 12 in reagent zone 4 typically provides a thickened diagnostic device when viewed from the side. (FIG. 2.) Particularly when the porous pad is non-absorbent, the porous pad 12 can provide a head pressure that helps flush the sample along the lateral flow membrane 10 to the detection zone 6 located downstream of the reagent zone 4.

The porous pad 12 comprises a material having a pore size greater in diameter than the diameter of the target microorganism (or cellular debris). The pore size of the porous pad is adequate for the passage of a target microorganism-antibody-detection reagent complex while still providing filtering of the sample. Generally, the pore size is at least about 50 times greater in diameter than the diameter of the target microorganism, typically about 100 times greater in diameter, preferably about 500 times greater in diameter and further preferably about 1000 times greater in diameter. For example, where the target microorganism is approximately 0.3 µm by 1 µm, the pore size is preferably at least 50 to 100 µm. The reagent zone 4, including the porous pad 12 when present, of the detection device is preferably disposed upon the lateral flow membrane, but may be also attached to the end of the lateral flow membrane.

In a preferred embodiment, as depicted in FIGS. 1 and 2, a control zone 20 is located downstream of the detection zone 6. The control zone 20 indicates the passage of material from the reagent zone 4, through the detection zone 6 and towards the absorbent pad 8. Preferably, the control zone 20 comprises a control antibody (or other binding partner) capable of binding a control chromogenic reagent previously located at the reagent zone 4. For example, the control chromogenic reagent may be avidin, and the control antibody/binding partner may be biotinylated BSA that is immobilized at the control zone 20. Other substances suitable for use in the control zone 20 are well known in the art, such as pH indicators, hydration indicators and other binding partners.

In another preferred embodiment, as depicted in FIGS. 1 and 2, the detection device further comprises an absorbent pad 8 located downstream of the control zone 20. The absorbent pad 8 typically acts as a sponge, absorbing fluid from the sample and thereby cause a greater portion of sample to migrate through the reagent zone 4, and across the detection zone 6. The absorbent pad 8 of the detection device is preferably disposed upon the lateral flow membrane, but may also be attached to the end of the lateral flow membrane.

Figure 3:
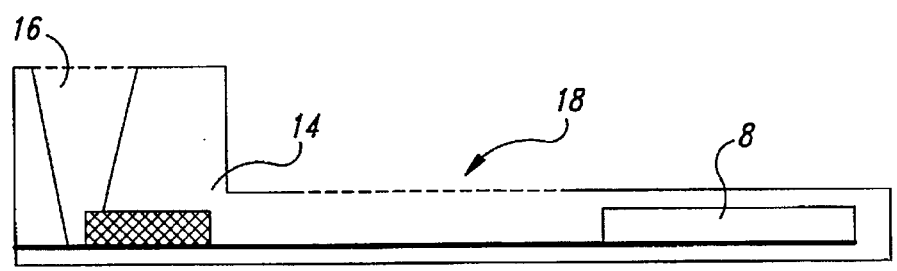
FIG. 3 depicts a side view of the lateral flow diagnostic device of the present invention enclosed within a case.

As depicted in FIG. 3, the diagnostic device is preferably enclosed within a case 14, such as a plastic case, for use in the field. The case 14 preferably has a conical opening 16 located adjacent or contacting the reagent zone. The conical opening provides for the funneling of sample to the reagent zone, as well as for measuring of the sample, if desired. The case 14 further comprises a window 18 located adjacent the detection zone 6, thereby providing for visual review and detection of a positive or a negative result at the detection zone 6. The window may also allow visual review of the control zone 20, or there can be a second window for the control zone 20. Typically, such detection is performed visually, although detection may also be performed by use of a reflectometer or other means known in the art.

Many other alternative embodiments of detection devices that, while not preferred, can be suitable for use with certain aspects of the claimed invention are known in the art and are depicted, for example, in U.K. Patent application No. 2,204, 398A, filed Apr. 25, 1988, and U.S. Pat. No. 4,943,522.

In a further aspect, the present invention provides a method of detecting a target microorganism wherein a solution comprising sample potentially containing the target microorganism is added to a reagent zone of a diagnostic device and contacting the sample with a mixture containing an antibody-detection reagent specific for the target microorganism and a composition as discussed above. Preferably, the composition comprises sucrose, BSA, and fish skin gelatin. In a preferred embodiment, the inventive composition does not include pyrrole, pyrrolidone or other pyrrole-related compounds. In an alternative embodiment, the composition also contains Tween 20 or Triton X100. The components of the composition are mixed together with the antibody-detection reagent prior to application of the mixture to the reagent zone of the diagnostic device (the components and the diagnostic device may be combined in another order, if desired).

Preferably, the sample is a solution containing, or consisting essentially of, an unpurified field sample such as a food sample, an environmental sample such as water or dirt. Alternatively, the sample may be a biological fluid such as a body fluid. In a lesser preferred embodiment, the sample may be purified prior to administration to the diagnostic device, such as a laboratory sample. Upon contacting the sample with the composition containing a specific antibody-detection reagent for the target microorganism that is potentially contained within the sample, binding between the antibody-detection reagent and the target microorganism is permitted.

In a highly preferred embodiment, the method further comprises filtering the sample (particularly where the sample is a field sample), by adding the sample to a porous, non-absorbent pad located within the reagent zone of the device.

Next, the antibody-detection reagent is permitted to bind to the target microorganism, and then the target microorganism-antibody-detection reagent complex is permitted to flow out of the reagent zone, and across a detection zone comprising a solid phase bound, immobile antibody capable of binding to the target microorganism-antibody-detection reagent complex. Preferably, the target microorganism-antibody-detection reagent complex is transported along the lateral flow membrane for a distance between the reagent zone and the detection zone.

The presence of the target microorganism-antibody-detection reagent complex at the detection zone is then detected. Such detection is usually done visually, although a reflectometer or other means known in the art may also be used for the detection.

The following Examples are offered by way of illustration, and not by way of limitation.

EXAMPLES

Example I

Salmonella

The following ingredients were mixed together in a clean container to encapsulate and allow for the flow of 20 nm colloidal gold particles attached to anti-Salmonella antibodies.

| Ingredients | Concentration |
| --- | --- |
| Sucrose | 10% |
| Bovine Serum Albumin | 2% |
| Gelatin | 0.25% |
| Tris buffer, pH 8.5 | 50 mM |
| NaCl | 100 mM |

Example II

Listeria

The following ingredients were mixed together in a clean container to encapsulate and allow for the flow of 0.3 μm dyed polystyrene particles attached to anti-Listeria antibodies.

| Ingredients | Concentration |
| --- | --- |
| Sucrose | 10% |
| Bovine Serum Albumin | 2% |
| Gelatin | 0.25% |
| Tris buffer, pH 8.5 | 50 mM |
| NaCl | 100 mM |

Example III

EHEC

The following ingredients were mixed together in a clean container to encapsulate and allow for the flow of 0.3 μm dyed polystyrene particles substituted with antibodies directed toward EHEC.

| Ingredients | Concentration |
| --- | --- |
| Sucrose | 2% |
| Bovine Serum Albumin | 1% |
| Gelatin | 0.5% |
| Tween 20 | 0.2% |
| Tris buffer, pH 8.5 | 50 mM |
| NaCl | 100 mM |

Example IV

Preparation of Diagnostic Device

The components of the composition as described above in Examples 1, 2 and 3, and the antibody-diagnostic reagent and a control reagent (avidin) were mixed and applied to a glass fiber pad having a pore size of at least 50–100 ∞m. The pad was then dried under reduced pressure at elevated temperature.

A capture antibody and a control antibody were applied to the detection zone and the control zone, respectively, of a strip of nitrocellulose having a pore size of about 8 μm using narrow-tipped pens with clean refillable cartridges. After air-drying the detection and control zones of the nitrocellulose strip, the remaining sites on the nitrocellulose were irreversibly blocked as known in the art, except with 5% fish skin gelatin. The nitrocellulose was then rinsed with distilled water and allowed to dry. The dried nitrocellulose was then placed on a glass slide, and the dried reagent pad was placed in overlapping relation with the nitrocellulose strip at the end closest to the detection zone. Chromatography paper was then placed in overlapping relation at the end of the nitrocellulose strip closest to the control zone.

Example V

Detection Of A Target Microorganism

A food sample or a pure culture sample potentially containing a target microorganism was added to a bacterial growth medium and incubated overnight. 100 μl to 250 μl of the sample solution were added to the reagent pad of the device prepared in Example IV. The addition of the sample rehydrated the absorbent pad and the components adhered thereto. The liquid comprising the sample and rehydrated components flowed out of the reagent pad and migrated through the nitrocellulose strip toward the absorbent pad made of chromatography paper.

As the liquid migrated, the antibody-diagnostic reagent bound to the target microorganism, providing an antibody-diagnostic reagent-target microorganism complex. Upon reaching the detection zone, the antibody-diagnostic reagent-target microorganism complex was bound by the capture antibody immobilized in the detection zone, resulting in a visibly detectable signal. Uncomplexed antibody-detection reagent and control reagent continued to migrate toward the absorbent pad. Upon reaching the control zone, the control reagent was bound to the control binding partner (biotinylated BSA), resulting in a visibly detectable signal in the control zone. All unbound reagents further migrated to the absorbent pad. Where the sample lacked the target microorganism, a visible signal was observed in the control zone but not in the detection zone. Positive results were obtained for samples containing each of Listeria, Salmonella and EHEC.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A lateral flow device for the detection of a whole or lysed target microorganism selected from the group consisting of yeast, bacteria, mold and fungi, said lateral flow device comprising, a lateral flow membrane having (a) a reagent zone comprising a porous pad containing a composition comprising about 0.1% to about 60% by weight of a polyol, up to about 25% by weight of a protein, about 0.1% to about 10% by weight of a gelatin and an antibody-detection reagent that specifically binds to said target microorganism, said porous pad having a pore size greater than the size of a complex between said target microorganism and said antibody-detection reagent, and (b) a detection zone located downstream of said reagent zone, said detection zone comprising an immobile binding partner capable of specifically binding said complex between said target microorganism and said antibody-detection reagent.

2. The device of claim 1 further comprising an absorbent pad capable of absorbing fluid on said lateral flow membrane and located downstream of said detection zone.

3. The device of claim 1 wherein said porous pad is non-absorbent.

4. The device of claim 1 wherein said porous pad is a glass fiber pad.

5. The device of claim 1 wherein said lateral flow membrane comprises nitrocellulose or nylon.

6. The device of claim 1 wherein said antibody-detection reagent is specific for Listeria.

7. The device of claim 1 wherein said antibody-detection reagent is specific for Enterohemorrhagic E. coli.

8. The device of claim 1 wherein said antibody-detection reagent is specific for Salmonella.

9. A method of detecting a whole or lysed target microorganism selected from the group consisting of yeast, bacteria, mold and fungi, said method comprising:

(a) contacting a sample potentially containing said target microorganism with a composition located in a reagent zone of a lateral flow membrane, said composition comprising about 0.1% to about 60% by weight of a polyol, up to about 25% by weight of a protein, about 0.1% to about 10% by weight of a gelatin and an antibody-detection reagent that specifically binds to said target microorganism, under conditions that permit said antibody-detection reagent to bind to said target microorganism to provide a complex between said target-microorganism and said antibody-detection reagent;

(b) migrating said complex downstream along said lateral flow membrane to a detection zone containing an immobile antibody capable of binding to said complex to provide a bound complex; and (c) detecting said bound complex.

10. The method of claim 9 wherein said sample is a solution comprising a field sample, and the method further comprises adding said sample to a porous, non-absorbent pad located in said reagent zone, said porous pad having a pore size greater than the size of said complex between said target microorganism and said antibody-detection reagent, and wherein said porous pad filters detritus from said field sample prior to said migrating.

11. The method of claim 10 wherein said field sample is selected from the group consisting of a food sample, an environmental sample and a biological fluid sample.

12. The method of claim 9 wherein said antibody-detection reagent is specific for Listeria.

13. The method of claim 9 wherein said antibody-detection reagent is specific for Enterohemorrhagic *E. coli*.

14. The method of claim 9 wherein said antibody-detection reagent is specific for Salmonella.

* * * * *

UNITED STATES PATENT AND TRADEMARK OFFICE
CERTIFICATE OF CORRECTION

PATENT NO. : 5,658,747
DATED : August 19, 1997
INVENTOR(S) : Philip T. Feldsine et al.

It is certified that error appears in the above-identified patent and that said Letters Patent is hereby corrected as shown below:

On the title page, Section 73, please delete "BioControl System, Inc." and insert therefore --BioControl Systems, Inc.--

Column 12, claim 9, line 50, please delete "target-microorganism" and insert therefore --target microorganism--.

Signed and Sealed this

Twenty-fifth Day of November, 1997

Attest:

BRUCE LEHMAN

*Attesting Officer*   Commissioner of Patents and Trademarks